(12) United States Patent  
Damay et al.

(10) Patent No.: US 7,947,864 B2
(45) Date of Patent: May 24, 2011

(54) LOW PROFILE ABSORBENT PANTILINER

(75) Inventors: Emmanuelle Cecile Damay, Erlangen (DE); Renee S. Kole, Neenah, WI (US); Lynn Marie Matheus, Appleton, WI (US); Ligia A. Rivera, Appleton, WI (US); Timothy James Van Himbergen, Appleton, WI (US); Margaret Gwyn Latimer, Alpharetta, GA (US); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1926 days.

(21) Appl. No.: 10/753,974

(22) Filed: Jan. 7, 2004

(65) Prior Publication Data

US 2005/0148969 A1    Jul. 7, 2005

(51) Int. Cl.
*A61F 13/15* (2006.01)
*A61F 13/20* (2006.01)

(52) U.S. Cl. ........................ 604/367; 604/378

(58) Field of Classification Search .................. 604/378, 604/367; 442/341, 349, 344, 393
See application file for complete search history.

(56) References Cited

U.S. PATENT DOCUMENTS

| 4,604,313 | A | * | 8/1986 | McFarland et al. ............ 428/172 |
| 4,657,538 | A | * | 4/1987 | Becker et al. ................. 604/381 |
| 4,862,574 | A | | 9/1989 | Seidy |
| 5,273,596 | A | | 12/1993 | Newkirk |
| 5,433,987 | A | | 7/1995 | Peterson et al. |
| 5,981,824 | A | | 11/1999 | Luceri |
| 6,395,957 | B1 | | 5/2002 | Chen et al. |
| 6,494,871 | B1 | | 12/2002 | Lariviere et al. |
| 6,635,039 | B1 | | 10/2003 | Levy |
| 6,705,189 | B2 | * | 3/2004 | Takai et al. .................... 428/137 |
| 2004/0253894 | A1 | * | 12/2004 | Fell et al. ....................... 442/381 |
| 2005/0079987 | A1 | * | 4/2005 | Cartwright et al. ........... 510/296 |

FOREIGN PATENT DOCUMENTS

| CA | 2 414 280 A1 | 12/2002 |
| EP | 0 070 164 A2 | 1/1983 |
| EP | 0 305 970 A2 | 3/1989 |
| EP | 0 625 602 A1 | 11/1994 |
| EP | 1 060 722 A2 | 12/2000 |

(Continued)

OTHER PUBLICATIONS

Lindsay, Jeffrey D. and Leonard H. Bieman, "Exploring Tactile Properties of Tissue With Moire Interferometry," Non-Contact, Three-Dimensional Gaging Methods and Technologies Workshop, Dearborn, Michigan, Mar. 1997.

(Continued)

*Primary Examiner* — Melanie J Hand
(74) *Attorney, Agent, or Firm* — Michael J. Bendel; Ralph H. Dean, Jr.

(57) ABSTRACT

A disposable absorbent liner for use in a crotch portion of underwear. The liner includes a cover layer having a top surface and an opposite bottom surface and comprising a mixture of hydrophilic microfibers and hydrophobic microfibers. A quantity of hydrophilic microfibers and hydrophobic microfibers are located at the top surface and a larger quantity of hydrophobic microfibers are located at the top surface than are a quantity of hydrophilic microfibers located at the top surface based on a total weight of the mixture of microfibers in the cover layer. The liner also includes a removable backing layer, and a liquid impermeable baffle layer having a top surface and an opposite bottom surface with the baffle layer being disposed between the cover layer and the backing layer. The absorbent liner has a low profile and a particular Absorbent Capacity and/or Absorbent Intake Rate.

21 Claims, 2 Drawing Sheets

FOREIGN PATENT DOCUMENTS

| WO | WO 92/07534 A2 | 5/1992 |
| WO | WO 01/67982 A2 | 9/2001 |
| WO | WO 02/47596 A1 | 6/2002 |

OTHER PUBLICATIONS

Lindsay, Jeffrey D. and Leonard H. Bieman, "Exploring Tactile Properties of Tissue With Moire Interferometry," Tappi Engineering and Papermakers Conference: Forming Bonds for Better Papermaking, Nashville, TN, Oct. 6-9, 1997, Tappi Press, vol. 2, pp. 979-992.

American Society for Testing Materials (ASTM) Designation: E 96-80, "Standard Test Methods for Water Vapor Transmission of Materials," pp. 742-751, published Feb. 1981.

* cited by examiner

LOW PROFILE ABSORBENT PANTILINER

BACKGROUND OF THE INVENTION

The present invention concerns personal hygiene products, more particularly, liners made to protect a user's underwear from staining. Liners are a class of absorbent articles (e.g., most often referred to as pantiliners for feminine use) designed to absorb small amounts of body fluids. They are smaller and more compact than conventional feminine sanitary napkins or pads. These products are designed to be flexible and soft and to protect the underwear of the user from staining. Liners can be shaped like an elongated oval and cover the underwear in the perineal area of the user, i.e., the crotch portion of the underwear. Alternatively, more modern designs for underwear, particularly women's panties known as "thong" or "tanga" or "string" or "boy shorts" panties, are unsuited for use with elongated-oval liner, but the same protection is still desired of the liner, and particularly since all of these more modern styles generally having less underwear in the crotch region than traditional underwear.

While various types of liners exist in the art, there remains a need for a liner product that may be used by a wearer frequently to protect underwear and which can still provide comfortable protection and reliable absorption of smaller amounts of fluid to help keep the user feeling dry, and advantageously across a range of liner designs which correspond to the more modern types of underwear worn. This would allow the consumer to cover her needs everyday between the periodic times when larger amounts of fluid absorption is needed, and keep her always feeling fresh. The applicants have surprisingly invented such an absorbent liner, as discussed further herein.

SUMMARY OF THE INVENTION

Various definitions used throughout the specification and claims are provided first, followed by a description of various aspects of the invention.

Definitions

As used herein, "disposable" means being disposed of after a single use and not intended to be washed and reused.

As used herein, "layer" means a mass of fibers or material having sufficient bonded integrity between the fibers or material in order to be maintained in a substantially coherent sheet when the sheet is used for its intended purpose.

As used herein, "hydrophilic" means fibers or surfaces of fibers that are wetted by aqueous liquids in contact with the fibers. The degree of wetting of the materials can be described in terms of contact angles and the surface tensions of the liquids and materials involved. Equipment and techniques suitable for measuring the wettability of particular fiber materials or blends of fiber materials can be provided by a Cahn SFA-222 Surface Force Analyzer System. When measured with this system, fibers having contact angles less than 90 degrees are designated "wettable", i.e., hydrophilic, and fibers having contact angles greater than 90 degrees are "non-wettable", i.e., hydrophobic.

As used herein, "hydrophobic" means fibers or surfaces of fibers that are not hydrophilic.

As used herein the term "nonwoven" means a layer of material having a structure of individual fibers or threads which are interlaid together, but not in an identifiable manner like a knitted fabric is so constructed. Nonwoven materials or layers have been formed from many processes such as for example, meltblowing processes, spunbonding processes, and bonded carded web processes. The basis weight of nonwoven material is usually expressed in ounces of material per square yard (osy) or grams per square meter (gsm) and the fiber diameters useful are usually expressed in microns (i.e., note that to convert from osy to gsm, multiply osy by 33.91).

As used herein the term "microfiber(s)" means small diameter fiber(s) having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about $1.42 (15^2 \times 0.89 \times 0.00707 = 1.415)$. Outside the United States the unit of measurement is more commonly the "tex", which is defined as the grams per kilometer of fiber. Tex may be calculated as denier/9.

As used herein, the term "low profile" means the Thickness of the disposable absorbent liner, or component thereof as applicable, determined according to the Thickness measurement in the Test Methods herebelow, and includes Thicknesses in the range of about 1 millimeter (mm) to greater than 0 mm.

As used herein, the term "machine direction (MD)" means the direction of travel of the forming surface onto which fibers are deposited during formation of a nonwoven fibrous material or layer.

As used herein, the term "cross-machine direction (CD)" means the direction which is essentially perpendicular to the machine direction and in the plane of the machine direction defined above.

"Bonded carded" refers to material or layers that are made from staple fibers which are sent through a combing or carding unit, which separates or breaks apart and aligns the staple fibers in the machine direction to form a generally machine direction-oriented fibrous nonwoven layer. This material may be bonded together to form a nonwoven layer by methods that include, without limitation, mechanical bonding such as needle punching, hydroentangling, and stitch bonding.

As used herein, the "WVTR" of a material is its water vapor transmission rate, which gives an indication of how comfortable a material may be to wear based on the breath ability of the material. WVTR is measured in accordance with ASTM Standard Test Method for Water Vapor Transmission of Materials, Designation E-96-80.

In response to the discussed difficulties and problems encountered in the art, a new liner has been invented that is a very thin or low profile absorbent article for every day use which provides light absorbency protection without sacrificing comfort. The low profile can be important because for every day use consumers want as little as possible to feel a foreign object between their body and their underwear, which tends to compromise their sense of freedom. When it comes to evaluating comfort, a key sensory signal consumers want is to keep their skin feeling dry. Thus, an absorbent product of the invention which can readily move body liquid or moisture (e.g., caused by sweat, vaginal discharge, slight urine loss, or the like) away from direct contact with the skin, connotes a feeling of freshness to the user. The purposes and features of the present invention will be set forth in and are apparent from the description that follows, as well as will be learned by practice of the invention. Additional features of the invention will be realized and attained by the product and process particularly pointed out in the written description and claims hereof, as well as from the appended drawings.

In one aspect, the invention provides a disposable absorbent liner for use in a crotch portion of underwear. The liner includes a cover layer having a top surface and an opposite bottom surface and comprising a mixture of hydrophilic microfibers and hydrophobic microfibers. A quantity of hydrophilic microfibers and hydrophobic microfibers are located at the top surface and a larger quantity of hydrophobic microfibers are located at the top surface than are a quantity of hydrophilic microfibers located at the top surface based on a total weight of the mixture of microfibers in the cover layer. The liner also includes a removable backing layer, and a liquid impermeable baffle layer having a top surface and an opposite bottom surface with the baffle layer being disposed between the cover layer and the backing layer. The absorbent liner has a low profile and an Absorbent Capacity in the range of about 2 grams to about 10 grams.

In another aspect, the invention provides a disposable absorbent liner for use in a crotch portion of underwear. The liner includes a cover layer having a top surface and an opposite bottom surface and comprising a mixture of hydrophilic microfibers and hydrophobic microfibers. A quantity of hydrophilic microfibers and hydrophobic microfibers are located at the top surface and a larger quantity of hydrophobic microfibers are located at the top surface than are a quantity of hydrophilic microfibers located at the top surface based on a total weight of the mixture of microfibers in the cover layer. The liner also includes a removable backing layer, and a liquid impermeable baffle layer having a top surface and an opposite bottom surface with the baffle layer being disposed between the cover layer and the backing layer. The absorbent liner has a low profile and an Absorbent Intake Rate of less than about 30 seconds.

In still another aspect, the invention provides a disposable absorbent liner for use in a crotch portion of underwear. The liner includes a cover layer having a top surface and an opposite bottom surface and comprising a mixture of hydrophilic microfibers and hydrophobic microfibers. A quantity of hydrophilic microfibers and hydrophobic microfibers are located at the top surface and a larger quantity of hydrophobic microfibers are located at the top surface than are a quantity of hydrophilic microfibers located at the top surface based on a total weight of the mixture of microfibers in the cover layer. The liner also includes a removable backing layer, and a liquid impermeable baffle layer having a top surface and an opposite bottom surface with the baffle layer being disposed between the cover layer and the backing layer. The absorbent liner has a low profile and an Absorbent Capacity in the range of about 2 grams to about 10 grams and an Absorbent Intake Rate of less than about 30 seconds.

In yet other aspects, the invention provides various configurations and optional features for the layers, as well as unique Density features not available in existing liners.

Various treatments may be applied to the cover layer to improve fluid transfer, although treatments only for improving fluid transfer may be advantageously excluded to save on manufacturing costs and/or generally provide a more readily skin friendly material, improve the environment near the user's skin or to actually improve the user's skin health.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the disposable absorbent liners of the invention.

BRIEF DESCRIPTION OF THE DRAWINGS

The drawings are merely representative and are not intended to limit the scope of the claims. Like parts depicted in the drawings are referred to by the same reference numerals.

DETAILED DESCRIPTION OF THE INVENTION

Absorbent liners of the present invention provide improved comfort, protection and absorbency in a liner product because they have a combination of properties, e.g., a relatively high density and/or a relatively high absorbent capacity and/or a relatively high intake rate, while maintaining a desired level of thickness or profile and flexibility that were not previously available in liners. The feel and performance of a liner is often characterized by one or more of the following attributes of the materials that comprise them: thickness, flexibility, texture, softness, absorbency, and barrier properties. In preparing a liner having a soft comfortable and dry feel and yet reasonably absorbent, it is important to balance the properties of the liner and its layers, e.g., low profile, Density, flexibility, Absorbent Rate and Absorbent Capacity. However, this is a difficult task because these properties can be interdependent, i.e., changing one property can adversely affect another property (and the overall feel and performance of the liner). Typically, when the thickness or profile is decreased, the absorbency (in terms of rate and/or capacity) is decreased. Differently, but equally concerning, typically when the basis weight is increased then the thickness is increased and the flexibility is decreased. Yet differently, but equally concerning, typically when the Density is increased, the absorbency (in terms of rate and/or capacity) is decreased. Thus, when a property is varied, to enhance the comfort/feel and absorbency, careful attention should be paid to the results obtained to avoid a resultant product having less desirable overall properties.

In light of these difficulties, through experimentation, the inventors have discovered certain properties to selectively isolate and vary to obtain a more comfortable and dry feel for a liner than before possible. In the present invention, the inventors have discovered the thickness can be maintained at a low profile and the absorbency can be increased while still maintaining a desirable flexibility. By way of example and without limitation, the absorbent liners of the invention can have properties and their ranges such as, for example, a low profile; an Absorbent Capacity (as determined in the Test Methods section herebelow) in the range of about 2 grams to about 10 grams and an Absorbent Intake Rate (as determined in the Test Methods section herebelow) of less than about 30 seconds. Alternatively or additionally, the absorbent liners of the invention can have properties and their ranges such as, for example, a Peak-to-Valley Depth (as determined in the Test Methods section herebelow) of about 0.1 mm to about 0.5 mm and a Peak-to-Peak Separation (as determined in the Test Methods section herebelow) between about 0.5 mm and about 3 mm.

Figure 1:
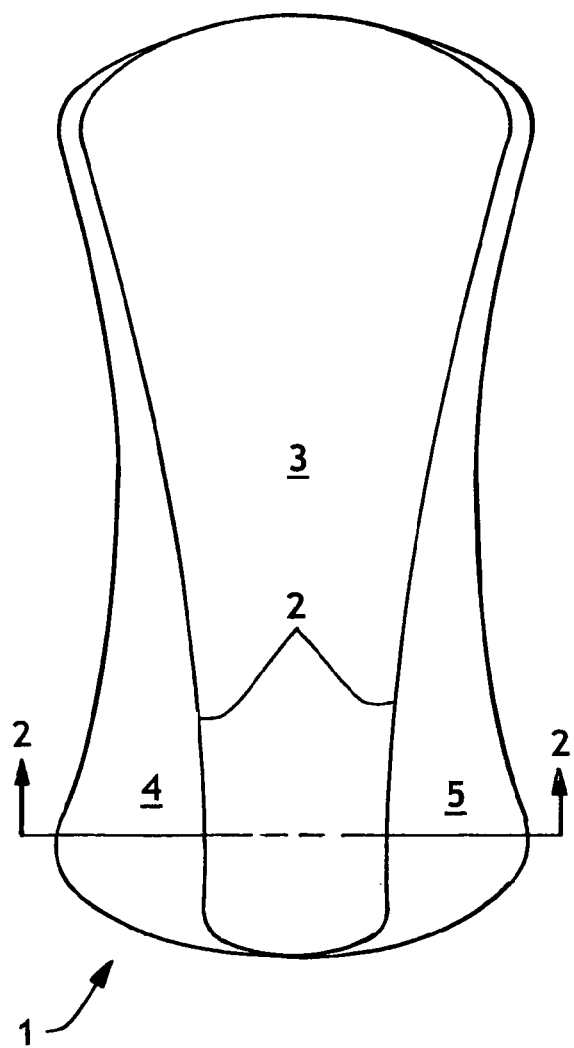
FIG. 1 is drawing of a liner 1 of the invention having an hourglass shape. The liner has a single line of embossing 2 corresponding approximately to the shape of a thong panty, that is used for folding the liner and that defines three separate areas of the liner; the central area 3 and the side areas 4, 5. The side areas can be folded under the panty along the fold (embossing) lines when used with a thong or other more modern panty.
Figure 2:
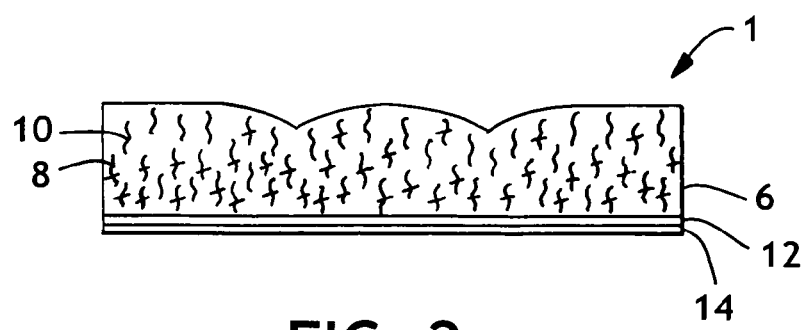
FIG. 2 is an enlarged cross section of the liner of FIG. 1, taken along the line 2-2, and where the relative proportional thickness of each layer of the liner to the other layers is depicted but each layer's exact thickness dimension is not so depicted.

Referring to the Figures, and FIGS. 1 and 2 for discussion now, there is depicted an disposable absorbent liner 1 for use in a crotch portion of underwear. The liner 1 includes a cover layer 6 having a top surface and an opposite bottom surface. The cover layer includes a mixture of hydrophilic microfibers and hydrophobic microfibers, where a quantity of the hydrophilic microfibers and the hydrophobic microfibers are located at the top surface but a larger quantity of hydrophobic microfibers are located at the top surface than are a quantity of hydrophilic microfibers located at the top surface based on a total weight of the mixture of microfibers in the cover layer. In this regard, for example, excellent results in low profile, Absorbent Capacity and Absorbent Intake Rate for a disposable absorbent liner have been found when the hydrophilic microfibers comprise greater than 65% and up to 80% of the microfibers based on a total weight of the mixture of microfibers in the cover layer and the hydrophobic microfibers comprise the remainder of the mixture of microfibers in the cover layer.

Without being limited to a particular theory of operation, it is believed that the particular distribution of these two types of fibers in the cover layer contribute to the absorbency of the layer, namely, the user facing side of the cover layer (the top surface of the cover layer) having a higher percentage of hydrophobic microfibers than the underwear facing side (the bottom surface of the cover layer) helps the user facing side remain relatively dry or feel relatively dry to the user, without the need for a highly hydrophobic surface that would hinder liquid or fluid intake. That is, the cover layer may advantageously have a z-direction gradient in microfiber composition, such that the user facing side of the cover layer is more hydrophobic than the underwear facing side of the cover layer, while still maintaining high Absorbent Intake Rates for a liner product. The relatively hydrophobic top surface of the cover layer in fluid communication with the more hydrophilic bottom surface of the cover layer aids the top surface to feel dry to a user while still providing an effective means for more readily wicking body liquid into the bottom portion of the cover layer and thus taking advantage of the full Absorbent Capacity of the cover layer. Stated slightly differently, the gradient structure in the liner of the invention can wick fluid or liquid toward the higher percentage of hydrophilic microfibers with relatively little impediment to the Absorbent Intake Rate and thus also enhancing the Absorbent Capacity through defined liquid management within the hydrophobic and hydrophilic microfiber mixture, i.e., and advantageously an integral matrix of the mixture of microfibers.

As another way to consider such features of the invention, the absorbent liner has a low profile and an Absorbent Capacity in the range of about 2 grams to about 10 grams. Advantageously, and in order of increasing advantage, the liner can have an Absorbent Capacity in the range of about 3 grams to about 9 grams or about 4 grams to about 8 grams, and combinations of either ends of the ranges here. Alternatively, or additionally, the absorbent liner has a low profile and an Absorbent Intake Rate of less than about 30 seconds. Advantageously, and in order of increasing advantage, the liner can have an Absorbent Intake Rate of less than about 20 seconds or less than about 10 seconds. Still alternatively, or additionally, the absorbent liner may have a Density greater than about 0.2 grams per cubic centimeter. Advantageously, and in order of increasing advantage, the liner can have a Density greater than about 0.225 grams per cubic centimeter or greater than about 0.25 grams per cubic centimeter.

Figure 3:
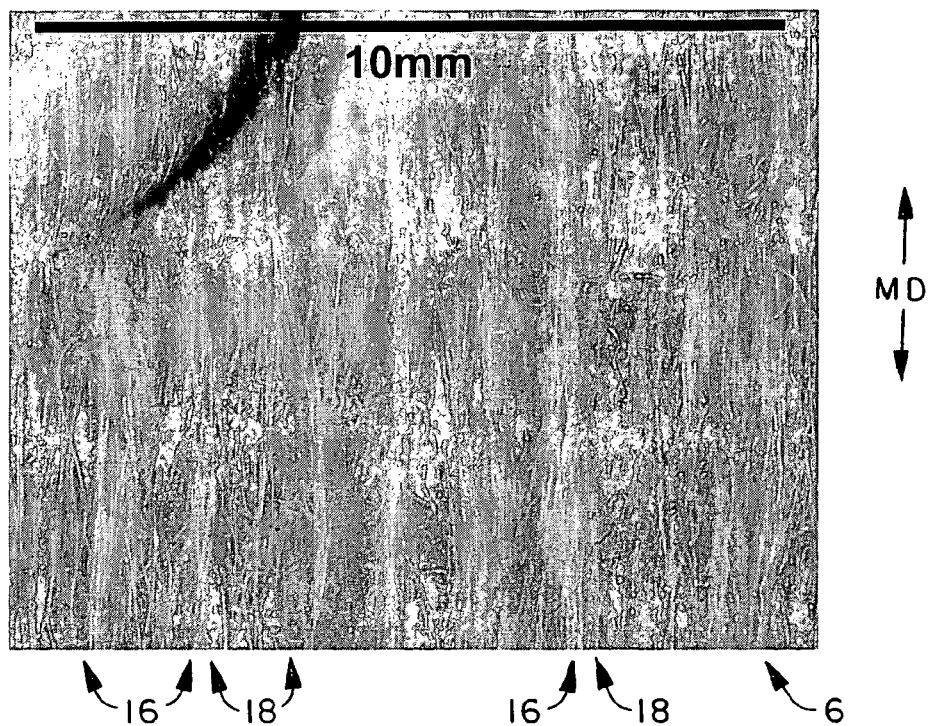
FIG. 3 is microscopy photograph of a portion of a top surface of a cover layer of an absorbent liner of the invention, taken under low angle reflected light and 12× magnification, and where the MD of the cover layer corresponds to the bottom-to-top and vice versa direction of the photograph.
Figure 4:
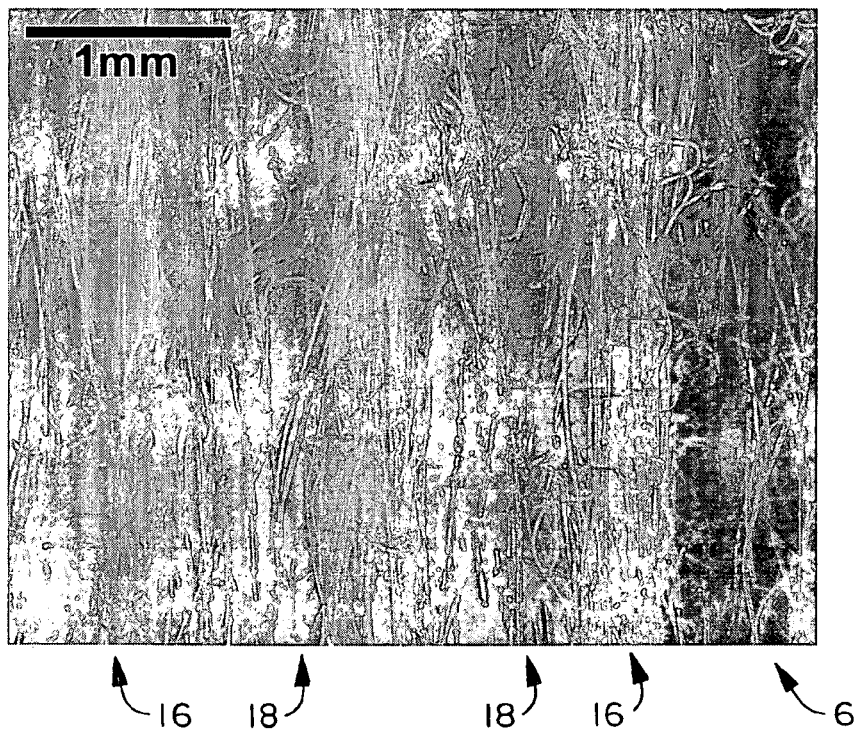
FIG. 4 is microscopy photograph of a portion of the portion of the top surface seen in FIG. 3, taken under low angle reflected light and 32× magnification.

Referring to FIGS. 3-4, another feature believed to contribute to the enhanced functionality of the liner, and particularly the cover layer, is now discussed. Particularly, there is depicted the microfibers at the top surface of the cover layer 6 formed into elongated MD peaks 16 and valleys 18 spaced apart from each other in the CD of the cover layer. Without being limited to a particular theory of operation, it is believed that MD fiber orientation is useful for distributing fluid in the longitudinal direction of the liner, resulting in more efficient use of the cover layer since more of the available pore volume therein will be filled during wicking before fluid reaches an edge or periphery of the liner (i.e., and assuming a source of liquid is applied centrally to the liner, which is most often the case in actual use) when the wicking region is elongated in the MD, as opposed to a less oriented structure that results in a more circular wicking region. Further, the defined peaks and valleys in the CD may provide large surface pores that facilitate fluid intake, relative to a structure with a much finer characteristic pore size on the surface of the web. Advantageously, and in order or increasing advantage, the cover layer can have a Peak-to-Valley Depth of the elongated MD peaks and valleys between about 0.1 mm and about 0.5 mm or between about 0.2 mm and about 0.4 mm. Advantageously, in combination or alternatively, and in order or increasing advantage, the cover layer can have a Peak-to-Peak Separation of the elongated MD peaks relative to the CD between about 0.5 mm and about 3 mm; between about 0.5 mm and about 2.5 mm, or between about 0.5 mm and about 2 mm.

Such a cover layer may be advantageous for light menstrual use or for delivery of medicaments, also. More sophisticated types of cover layers may incorporate treatments of lotions or medicaments to improve the environment near the skin or to actually improve skin health. Such treatments include aloe, vitamin E, baking soda and other preparations as may be known or developed by those skilled in the art.

The hydrophilic microfibers and hydrophobic microfibers may be either synthetic fibers or natural filers, as long as they have the desired wettability or nonwettability, and the cover may be formed as a bonded carded layer. Synthetic fibers include those made from polyolefins, polyamides, polyesters, rayon, acrylics, superabsorbents, LYOCELL® regenerated cellulose and any other suitable synthetic fibers known to those skilled in the art. Many polyolefins are available for fiber production, for example polyethylenes such as Dow Chemical's ASPUN® 6811A liner low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENES PD 3445 polypropylene and Montell Chemical Co.'s PF304. Other polyolefins are also available.

Natural fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Crimping may be imparted to the fibers, e.g., by conventional means. Curl may be imparted to the fibers, e.g., by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

Again referring to FIG. 2, the liner also includes a removable backing layer 14, and a liquid impervious baffle layer 12 having a top surface and an opposite bottom surface with the baffle layer being disposed between the cover layer and the backing layer. The top surface of the baffle layer may be secured to the bottom surface of the cover or there may be another layer(s) or materials therebetween as taught herein. Alternatively or additionally, the backing layer may be removably secured to the bottom surface of the baffle layer or there may be another layer(s) or materials therebetween as taught herein.

The baffle layer is impermeable to liquid in order to keep the clothing or underwear of the wearer from becoming soiled. The impermeable baffle layer is preferably made from a thin film and is generally made from plastic though other materials may be used. Nonwoven layers, films or film coated nonwovens may be used as the baffle as well. Suitable film compositions for the baffle include polyethylene film which may have an initial thickness of from about 0.5 mil (0.012 millimeter) to about 5.0 mil (0.12 millimeter). The baffle layer may optionally be composed of a vapor or gas permeable, microporous "breathable" material that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Other suitable thermoplastic materials like other olefins, nylons, polyesters or copolymers of, for example, polyethylene and polypropylene may also be used.

Advantageously, while being absorbent, the absorbent liner of the invention does not include a core portion, such as do conventional sanitary napkins or pads of personal care products designed to absorb larger amounts of liquid and secondarily to contain solids. Without a core, the invention can provide greater comfort to a user with less awareness of the absorbent liner that is located between the user and his/her underwear. However, various other layers may be included in absorbent liners of the invention provided the desired feature(s) of the invention can still be obtained. Such other layers may be surge layers, and may be placed between the cover layer and the baffle layer and designed, as the name suggests, to contain surges of liquid so that the cover layer core may absorb the amount of liquid more evenly over time. Distribution layers may also be included in the invention. Distribution layers may be located next to the cover layer and accept liquid from the surge layer and distribute it to other areas of the cover layer. In this manner, rather than absorbing liquid exclusively in the vicinity of initial impact upon the cover layer, more of the absorbent cover layer is used throughout the absorbent liner.

Adhesive (not shown), or other similar functioning materials for attaching the absorbent liner 1 to underwear, may be applied to at least a portion of the bottom surface of the baffle layer 12 to keep the liner it in place while in use. The adhesive may be applied in any effective pattern. The adhesive may, for example, be applied as a narrow strip down the center, a wide strip covering the liner in a rectangular shape with a width equal to the width of the liner at its narrowest point, or may cover the entire liner backing. A narrower strip of adhesive is advisable for more breathable embodiments since the adhesive tends to detract from breath ability. If the adhesive is applied as a narrow strip in the center area 3, additional adhesive may be applied to the backing under the side areas 4, 5.

A removable backing layer 14, e.g., peel able or detachable paper, is applied to the adhesive on the bottom surface of the baffle layer. The backing layer 14 is removed from the adhesive by the user prior to application of the liner to the panty.

The instant invention also includes a convertible, disposable absorbent liner that may be used with conventional underwear or with thong style panties or underwear. The liner 1, as shown in FIG. 1, has a slightly "hourglass" shape. It has a single line of embossing 2 corresponding approximately to the shape of a thong panty, that is used for folding the liner and that defines three separate areas of the liner. The central area 3 is in absorbent service when the liner is applied to either style of panty. The periphery includes side areas 4, 5 that are in absorbent service when the liner is applied to a conventional, hourglass-shaped panty but are folded under the panty along the fold (embossing) lines 2 when used with a thong panty. It is possible to have additional lines of embossing for folding on either side of the single line shown in FIG. 1, and attention is directed to a pending application of the assignee of the present application, titled "DUAL-USE PANTILINER" and published Jun. 20, 2002 as WO 02/47596.

EXAMPLE

The cover layer was prepared from a first concentration of carded microfibers having a relatively homogenous mixture of 80% polypropylene microfibers and 20% rayon microfibers (27 gsm) being combined over a second concentration of carded microfibers having a relatively homogenous mixture of 100% rayon microfibers (53 gsm). All the microfibers of this example were 1.7 in denier and 40 mm long, although other fiber denier and lengths could readily be used. Also, the microfibers were crimped as discussed herein, and single component fibers although uncrimped and/or bi-component fibers could be used. The concentrations of microfibers are then supported on a foraminous belt while they are subjected to a high pressure hydro entangling process to form a bonded carded cover layer of 80 gsm. A vacuum may be located beneath the foraminous belt so that excess fluid may be withdrawn from the hydroentangled layer. After entanglement, the layer is transferred to a non-compressive drying operation. The cover layer keeps the skin dry, or at least feeling dry, during usage through concentrating the hydrophobic fibers towards the body side of the cover layer. The basis weight for the cover layer of this example results in the hydrophobic fibers being about 30% of the total weight of microfibers in the layer, leaving 70% to the hydrophilic microfibers.

The cover layer was then embossed separately. Since the cover layer is so thin, the embossing gap is nearly immeasurable, meaning that the pattern roll and anvil roll are nearly touching to provide a quality-embossing pattern. The baffle layer and cover layer are not embossed together, because the baffle layer is susceptible to cut-through from the embosser at such a small process gap. Fold lines consistent with WO 02/47596 were used to provide a dual fit for regular and thong panties.

The machine direction (MD) flexibility and cross direction (CD) flexibility for the cover layer were not equal. The MD was less flexible than the CD to a ratio that aids the WO 02/47596 embossed fold lines. When the MD and CD flexibilities of the cover layer are equal, the WO 02/47596 fold lines may not fold easy due to the lack of directional rigidity in the material to orientate the fold along the embossed line. A typical CD/MD is greater than 29%.

Next, a fragrance was applied to the bottom side of the cover layer. A pressurized tank supplied a constant pressure to an applicator. The add-on was controlled by the timing in the applicator. The spray application system used 100% wool felt to cushion the spray velocity as the fragrance was atomized. As the machine ran, the felt was saturated with fragrance, which then transferred the fragrance to the cover layer. The fragrance was an oil-based compound that was diluted 2:1 in Isopropyl Myristate. The specific gravity was around 0.846-0.854 with a viscosity range of 4-5 mPas at 25° C. Natural extracts, such as, lavender, chamomile, aloe vera and green tea made up each fragrance grade to provide natural freshness for everyday usage.

After the fragrance application, the baffle layer (of 40 gsm) was laminated with hot melt adhesive through either continuous filament swirls or slot coat application. The baffle layer was a film (e.g., about 0.15 mm thick) impermeable to liquid passage to keep soiled materials away from the panty of the user. The impermeable baffle layer was a thin film made mostly of polyethylene, although other polymers may be used for this film also. The baffle film was impermeable to liquid, but breathable through imbedding fillers into the polymer formulation. The baffle film was extruded and then stretched in the MD. During this stretch process, voids were created around the filler particles to make the film "breath". The basis weight range for the film was 30-50 gsm.

After the cover layer and baffle layer were laminated, garment adhesive and a backing layer (e.g., peel paper strip of about 0.06 mm) were adhered to the bottom side of the baffle layer. The garment adhesive has properties of high attachment cohesion to fabric materials with low residue after removal. The garment adhesive was slot coated to the paper peel strip and then both adhesive and peel paper was laminated to the baffle layer.

The product was then cut by a die into an hourglass shape to the dimensions of 150 mm long, 57 mm wide at the lobes (CD) and 44 mm wide at the center (CD). The liner product Thickness was about 0.70 mm.

This product was produced in the hourglass shape of a liner as shown in FIG. 1 so that it could be applied to a conventional panty with this shape. It was found that this product was easily converted into use as a thong liner by bending the side areas downward and wrapping them around the panty. The absorbent liner product had: a low profile of 0.80 mm; a Basis Weight of 200 gsm; a Density of 0.25 g/cc; an Absorbent Capacity of 5.38 g and an Absorbent Intake Rate of 8.5 sec.; all as determined-according to the Test Methods herebelow.

Test Methods

The testing set forth herein is performed where absorbent liner, or portion thereof as applicable, samples are conditioned 24 hours and tested under TAPPI standard conditions of 23±1° C. and 50±2% RH. The test equipment discussed is exemplary and should be used to conduct the testing, however, alternative equipment that is equivalent in all material respects for the given test can be used also (but in the event of conflict between test results the test results from the exemplary equipment shall control).

Thickness Measurement

The "Thickness" of an absorbent liner, or its layer(s) as applicable, of the invention is found using the Compression Tester model KES-FB-2 manufactured by Kato Tech Co., Ltd in Japan. The thickness of a sample is found by a single cycle compression of the sample between two circular stainless steel plungers of an area of 2 cm$^2$ each. The velocity of compression is 20 micron/sec. When the pressure attains a level of 50 grams force/cm$^2$ (gf/cm$^2$) the top plunger retracts at the same velocity of 20 micron/sec. and recovery of the compressed material begins. The thickness is taken during the compression of the sample at the pressure of 0.5 gf/cm$^2$ as the plungers first move towards each other. This test is conducted on a finished liner sample where the center of the test plunger is placed over the center of the sample liner (center point between its longitudinal ends and center point between its widthwise sides). Five samples are tested in this manner and the thickness to the closest hundredth of a millimeter for each sample is added together and the collective total thickness divided by 5, which thereby determines the Thickness of the liner, or its layer(s) as applicable, which is discussed herein and set forth in the claims.

Absorbent Capacity Measurement

The "Absorbent Capacity" of an absorbent liner of the invention is found using by loading a sample liner product with a saline liquid (i.e., distilled water at 0.9±0.005% saline concentration), allowing the sample to absorb the liquid and measuring the point at which the saline liquid begins to leak off the sides or ends, whichever occurs first. A conventional average diameter syringe with 60 mL of saline liquid therein is obtained. The sample liner is laid flat with the body side facing up on a horizontal work surface large enough to support the sample and provide at least a 2.5 cm empty periphery work surface surrounding the sample. The sample is then uniformly insulted with the saline liquid in the MD direction (length of sample) with a continuous sweeping motion. Close attention is paid for uniform insulting with the saline liquid. Saline liquid flow from the syringe is stopped when visual inspection indicates saline liquid begins to leak from a side or end of the sample, whichever occurs first. The absorbent capacity of the sample is the initial saline liquid volume (in grams) in the syringe minus the final saline liquid volume (in grams) left in the syringe once saline liquid flow from the syringe is stopped. A statistically significant number of samples (e.g., 10) are tested in this manner and the absorbent capacity for each sample is added together and the collective total divided by ten, which thereby determines the average absorbent capacity (in grams) of the absorbent liner. The average absorbent capacity is then multiplied by the result of dividing 75.2 square centimeters by the surface area (in square centimeters) of the top surface of the sample liner (i.e., by determining the average surface area of the ten samples tested for absorbent capacity), and this determines the Absorbent Capacity (in grams) of the absorbent liner which is discussed herein and set forth in the claims.

Absorbent Intake Rate Measurement

The "Absorbent Intake Rate" of an absorbent liner of the invention is found by determining the time, to the nearest second, until a specified amount of saline liquid (i.e., distilled water at 0.9±0.005% saline concentration) is absorbed into a sample absorbent liner. The following equipment is used: a conventional syringe pump capable of delivering flow rate of 1 mL/per 5 seconds. Syringe at least 5 mL capacity for saline liquid. A timing device, such as digital, readable to 1 second or less, e.g., stopwatch, VWR Scientific Products part number 62379-218, or equivalent. Sufficient saline liquid. The sample is prepared as follows: sample liner remove from the product pouch or packaging, being careful not to stretch or flatten the product, but do lay it flat with the body side facing up on a horizontal work surface large enough to support the sample and provide at least a 2.5 cm empty periphery work surface surrounding the sample. This test is conducted on a finished liner sample where the center of the test plunger is placed over the center of the sample liner (center point between its longitudinal ends and center point between its widthwise sides). For the syringe pump, refer to the manufacturer's instruction manual for the key sequences used to program the syringe pump. Each product should receive a total of 1 mL of saline liquid over the insult period. Program the syringe pump to deliver 1 mL of simulant at a rate of 1 mL/per 5 seconds. Start delivery of the saline liquid and the stop watch simultaneously. Manually monitor the progress of the saline liquid. When the saline liquid has completely absorbed into the specimen (i.e., there is not liquid visibly resting on top between voids in the fibers of the top surface) stop the timing device. Record the time to the nearest second as the absorbent intake rate. A statistically significant number of samples (e.g., 10) are tested in this manner and the absorbent intake rate for each sample is added together and the collective total divided by ten, which thereby determines the Absorbent Intake Rate of the absorbent liner which is discussed herein and set forth in the claims.

Basis Weight Measurement

The Basis Weight (in grams per square meter, $g/m^2$ or gsm) of an absorbent liner, or its components as applicable, is calculated by dividing the dry weight by the area (in square meters) after manufacture of the liner and before coating with any additive or treatment. A statistically significant number of samples (e.g., 10) are tested in this manner and the basis weight for each measured sample is added together and the collective total divided by the total number of samples measured, which thereby determines the Basis Weight of the absorbent liner, or its components as applicable, which is discussed herein and set forth in the claims.

Density Measurement

The Density of an absorbent liner, or its applicable components, is a "dry density" and is calculated as the Basis Weight (in grams per square meter, $g/m^2$ or gsm) divided by the Thickness of the liner, or its applicable components, after manufacture and before coating with any additive or treatment. A statistically significant number of samples (e.g., 10) are tested in this manner and the density for each measured sample is added together and the collective total divided by the total number of samples measured, which thereby determines the Density of the absorbent liner, or its components as applicable, which is discussed herein and set forth in the claims.

Peak-to-Valley Depth Measurement

The "Peak-to-Valley Depth" of an absorbent liner of the invention is found using the CADEYES optical moiré interferometry approach described in U.S. Pat. No. 6,395,957, issued May 28, 2002 to Chen et al., but using a 5-mm field of view device instead of a 38-mm field of view device, as further described in J. D. Lindsay and L. Bieman, "Exploring Tactile Properties of Tissue with Moiré Interferometry," *Proceedings of the Non-contact, Three-dimensional Gaging Methods and Technologies Workshop*, Society of Manufacturing Engineers, Dearborn, Mich., Mar. 4-5, 1997; and, in J. D. Lindsay and L. Bieman, "Exploring Tactile Properties of Tissue with Moiré Interferometry," *Proceedings of the Tappi Engineering and Papermakers Conference: Forming Bonds for Better Papermaking*, Nashville, Tenn., Oct. 6-9, 1997, Tappi Press, Atlanta, Ga., Vol. 2, pp. 979-992. A statistically significant number of samples (e.g., 10) are tested in this manner and the peak-to-valley depth for each measured peak-to-valley is added together and the collective total divided by the total number of peak-to-valley measurements made, which thereby determines the Peak-to-Valley Depth of the elongated MD peaks spaced apart from each other in the CD of the cover layer of the absorbent liner, which is discussed herein and set forth in the claims.

Peak-to-Valley Separation Measurement

The "Peak-to-Valley Depth" of an absorbent liner of the invention is found using the CADEYES optical moiré interferometry approach described in U.S. Pat. No. 6,395,957, issued May 28, 2002 to Chen et al., but using a 5-mm field of view device instead of a 38-mm field of view device, as further described in J. D. Lindsay and L. Bieman, "Exploring Tactile Properties of Tissue with Moiré Interferometry," *Proceedings of the Non-contact, Three-dimensional Gaging Methods and Technologies Workshop*, Society of Manufacturing Engineers, Dearborn, Mich., Mar. 4-5, 1997; and, in J. D. Lindsay and L. Bieman, "Exploring Tactile Properties of Tissue with Moiré Interferometry," *Proceedings of the Tappi Engineering and Papermakers Conference: Forming Bonds for Better Papermaking*, Nashville, Tenn., Oct. 6-9, 1997, Tappi Press, Atlanta, Ga., Vol. 2, pp. 979-992. A statistically significant number of samples are tested in this manner and the peak-to-peak separation for measured adjacent peaks is added together and the collective total divided by the total number of adjacent peaks measured, which thereby determines the Peak-to-Peak Separation of the elongated MD peaks relative to the CD for the cover layer of the absorbent liner, which is discussed herein and set forth in the claims.

All publications, patents, and patent documents cited in the specification are incorporated by reference herein, as though individually incorporated by reference. In the case of any inconsistencies, the present disclosure, including any definitions herein, will prevail. While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

What is claimed is:

1. A disposable absorbent liner for use in a crotch portion of underwear comprising:

a cover layer having a top surface and an opposite bottom surface, the cover layer comprising a mixture of hydrophilic microfibers and hydrophobic microfibers, wherein a quantity of hydrophilic microfibers and hydrophobic microfibers are located at the top surface and a quantity of hydrophobic microfibers located at the top surface is larger than a quantity of hydrophilic microfibers located at the top surface, based on a total weight of the mixture of microfibers in the cover layer;
a removable backing layer;
a liquid impermeable baffle layer having a top surface and an opposite bottom surface with the baffle layer being disposed between the cover layer and the backing layer; and,
wherein the absorbent liner has a low profile and an Absorbent Capacity in the range of about 2 grams to about 10 grams.

2. A disposable absorbent liner for use in a crotch portion of underwear comprising:
a cover layer having a top surface and an opposite bottom surface, the cover layer comprising a mixture of hydrophilic microfibers and hydrophobic microfibers, wherein a quantity of hydrophilic microfibers and hydrophobic microfibers are located at the top surface and a quantity of hydrophobic microfibers located at the top surface is larger than a quantity of hydrophilic microfibers located at the top surface, based on a total weight of the mixture of microfibers in the cover layer;
a removable backing layer;
a liquid impermeable baffle layer having a top surface and an opposite bottom surface with the baffle layer being disposed between the cover layer and the backing layer; and,
wherein the absorbent liner has a low profile and an Absorbent Intake Rate of less than about 30 seconds.

3. A disposable absorbent liner for use in a crotch portion of underwear comprising:
a cover layer having a top surface and an opposite bottom surface, the cover layer comprising a mixture of hydrophilic microfibers and hydrophobic microfibers, wherein a quantity of hydrophilic microfibers and hydrophobic microfibers are located at the top surface and a quantity of hydrophobic microfibers located at the top surface is larger than a quantity of hydrophilic microfibers located at the top surface, based on a total weight of the mixture of microfibers in the cover layer;
a removable backing layer;
a liquid impermeable baffle layer having a top surface and an opposite bottom surface with the baffle layer being disposed between the cover layer and the backing layer; and,
wherein the absorbent liner has a low profile and an Absorbent Capacity in the range of about 2 grams to about 10 grams and an Absorbent Intake Rate of less than about 30 seconds.

4. The absorbent liner of claims 1, 2 or 3 wherein the top surface of the baffle layer is secured to the bottom surface of the cover.

5. The absorbent liner of claims 1, 2 or 3 wherein the backing layer is removably secured to the bottom surface of the baffle layer.

6. The absorbent liner of claims 1, 2 or 3 wherein the top surface of the baffle layer is secured to the bottom surface of the cover and the backing layer is removably secured to the bottom surface of the baffle layer.

7. The absorbent liner of claims 1 or 3 wherein the Absorbent Capacity is between about 3 grams and about 9 grams.

8. The absorbent liner of claim 7 wherein the Absorbent Capacity is between about 4 grams and about 8 grams.

9. The absorbent liner of claims 2 or 3 wherein the Absorbent Intake Rate is less than about 20 seconds.

10. The absorbent liner of claim 9 wherein the Absorbent Intake Rate is less than about 10 seconds.

11. The absorbent liner of claims 1, 2 or 3 wherein the absorbent liner has Density greater than about 0.2 grams per cubic centimeter.

12. The absorbent liner of claim 11 wherein the absorbent liner has Density greater than about 0.225 grams per cubic centimeter.

13. The absorbent liner of claim 11 wherein the absorbent liner has Density greater than about 0.25 grams per cubic centimeter.

14. The absorbent liner of claims 1, 2 or 3 wherein the liner comprises a periphery and at least one fold line defining a central area and two side areas, wherein the liner may be adjusted in size by folding the liner along the fold line.

15. The absorbent liner of claims 1, 2 or 3 wherein an underwear attaching material is provided on at least a portion of the bottom surface of the baffle layer.

16. The absorbent liner of claims 1, 2 or 3 wherein the cover layer is a nonwoven integral matrix of the mixture of microfibers.

17. The absorbent liner of claims 1, 2 or 3 wherein the microfibers at the top surface of the cover layer are formed into elongated MD peaks and valleys spaced apart from each other in the CD.

18. The absorbent liner of claim 17 wherein the Peak-to-Valley Depth of the elongated MD peaks and valleys is between about 0.1 mm and about 0.5 mm.

19. The absorbent liner of claim 17 wherein the Peak-to-Peak Separation of the elongated MD peaks relative to the CD is between about 0.5 mm and about 3 mm.

20. The absorbent liner of claim 18 wherein the Peak-to-Peak Separation of the elongated MD peaks relative to the CD is between about 0.5 mm and about 3 mm.

21. The absorbent liner of claims 1, 2 or 3 wherein the hydrophilic microfibers comprise greater than 65% and up to 80% of the microfibers based on a total weight of the mixture of microfibers in the cover layer and the hydrophobic microfibers comprise the remainder of the mixture of microfibers in the cover layer.

* * * * *